United States Patent

Wakatsuki et al.

Patent Number: 4,774,350
Date of Patent: Sep. 27, 1988

[54] PHOSPHORIC ESTER

[75] Inventors: Junya Wakatsuki; Tohru Katoh, both of Wakayama; Tomihiro Kurosaki, Osaka, all of Japan

[73] Assignee: Kao Corporation, Tokyo, Japan

[21] Appl. No.: 896,100

[22] Filed: Aug. 13, 1986

[30] Foreign Application Priority Data

Aug. 30, 1985 [JP] Japan .................................. 60-191134

[51] Int. Cl.$^4$ ............................................. C07F 9/09
[52] U.S. Cl. ................................................. 558/169
[58] Field of Search ............................ 558/169, 109

[56] References Cited

U.S. PATENT DOCUMENTS 3,034,349  2/1967  Shen ........................... 558/169
4,623,743  11/1986  Kurosaki et al. ............ 558/169

Primary Examiner—Anton H. Sutto
Attorney, Agent, or Firm—Oblon, Fisher, Spivak, McClelland & Maier

[57] ABSTRACT

Novel phosphoric esters represented by the following general formula (I)

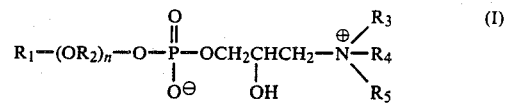

wherein $R_1$ represents a linear or branched alkyl or alkenyl group having 1 to 36 carbon atoms, or a phenyl group substituted with a linear or branched alkyl group having 1 to 15 carbon atoms, $R_2$ represents an alkylene group having 2 to 3 carbon atoms, $R_3$, $R_4$ and $R_5$ individually represent a hydrogen atom or a linear or branched alkyl group having 1 to 36 carbon atoms providing that any one of $R_3$, $R_4$ and $R_5$ has 5 or more carbon atoms, and n is a number from 0 to 30 are obtained by reacting phosphoric esters of the following formula

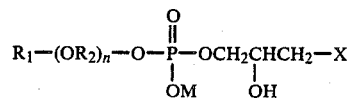

with amines at a high purity and in a high yield.

The phosphoric esters (I) are excellent in the surface tension and foaming property, and give extremely low stimulus to the skin, so that they can be utilized in detergent compositions, cosmetic compositions, emulsifiers, dispersants, anti-static agents and the like.

2 Claims, 1 Drawing Sheet

PHOSPHORIC ESTER

BACKGROUND OF THE INVENTION

1. Field of the Invention

This invention concerns a novel phosphoric ester and, more specifically, it relates to a phosphoric ester represented by the following general formula (I):

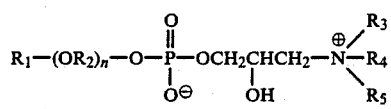

wherein $R_1$ represents a linear or branched alkyl or alkenyl group having 1 to 36 carbon atoms, or a phenyl group substituted with a linear or branched alkyl group having 1 to 15 carbon atoms, $R_2$ represents an alkylene group having 2 to 3 carbon atoms, $R_3$, $R_4$ and $R_5$ individually represent a hydrogen atom or a linear or branched alkyl group having 1 to 36 carbon atoms providing that any one of $R_3$, $R_4$ and $R_5$ has 5 or more carbon atoms, and n is a number from 0 to 30.

2. Description of the Prior Art

Phosphoric esters have been utilized in various fields as detergents, fiber processing agents, emulsifiers, rust inhibitors, liquid ion exchangers or pharmaceuticals.

For the detergents, alkyl sulfates, alkylbenzene sulfonates, α-olefin sulfonates and the likes have hitherto been used. However, since many of these surface active agents roughen the skin, it has been demanded to provide such detergents causing less irritations to the skin. Recently, phosphoric monoester salts have been used as less stimulating surface active agents.

The living body contains various phosphate type surfactants having quaternary ammonium salts in one molecule and referred to as a phospholipid. Lecithin and phosphatidyl serine are typical examples of the phospholipid. These phospholipids are utilized in various fields because of their surface activity, emulsifying ability and physiological properties. In view of this, it is expected that those substances having structures similar to the phospholipids are less stimulative to the living body as compared with the aforementioned phosphoric acid monoester salts, and syntheses of various phospholipid-like substances have been conducted. However, since the syntheses often require multi-step reactions, yields for most of aimed products are often low (E. Baer, et al., Journal of the American Chemical Society, 72, 942 (1950)).

Under the above circumstances, several of the present inventors succeeded in obtaining a novel compound having a quaternary ammonium salt in one molecule represented by the following formula in a simple procedure:

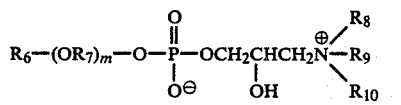

wherein $R_6$ represents a linear or branched saturated or unsaturated hydrocarbon group which may possibly be substituted and having from 8 to 32 carbon atoms, $R_8$, $R_9$ and $R_{10}$, which may be different or identical with other, represent individually a saturated or unsaturated hydrocarbon group having 1 to 4 carbon atoms, $R_7$ represents an alkylene group having 2 to 3 carbon atoms and m represents an integer from 0 to 50 (Japanese Patent Application No. 39042/1984). More particularly, they found that the compound can be produced easily by reacting a monoalkali metal salt of a monoalkylphosphoric acid represented by the formula (III) with a glycidyltrialkyl ammonium salt represented by the formula (IV) in accordance with the following reaction scheme and that a representative compound, dodecyl-2-hydroxy-3-N,N,N-trimethylammoniopropyl phosphate ($R_6=C_{12}H_{25}$, $R_8=R_9=R_{10}=CH_3$, and m=0 in the compound (II)) has an excellent deterging effect and extremely low stimulation to the living body.

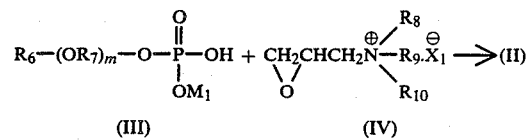

wherein $M_1$ represents an alkali metal, $X_1$ represents an anion and $R_6$, $R_7$, $R_8$, $R_9$, $R_{10}$ and m have the same meanings as described above.

However, among the glycidyltrialkyl ammonium salts, only glycidyltrimethyl ammonium chloride is industrially available at present and it has been difficult to industrially obtain those compounds having various alkyl ammonio groups.

SUMMARY OF THE INVENTION

In view of the foregoing situations, the present inventors have made an earnest study and, as a result, have accomplished this invention on the findings that not only the phosphoric ester represented by the formula (II) but also a novel phosphoric ester represented by the formula (I) can be obtained in simple procedures, at a high purity and in a high yield by using starting materials available economically and easily.

Accordingly, this invention provides a novel phosphoric ester represented by the formula (I).

BRIEF DESCRIPTION OF THE DRAWING

The sole FIGURE is a chart illustrating infrared absorption spectrum for dodecyl 2-hydroxy-3-N,N-dimethyl-N-dodecyl-ammoniopropyl phosphate.

DETAILED DESCRIPTION OF THE INVENTION AND PREFERRED EMBODIMENTS

Figure 1:
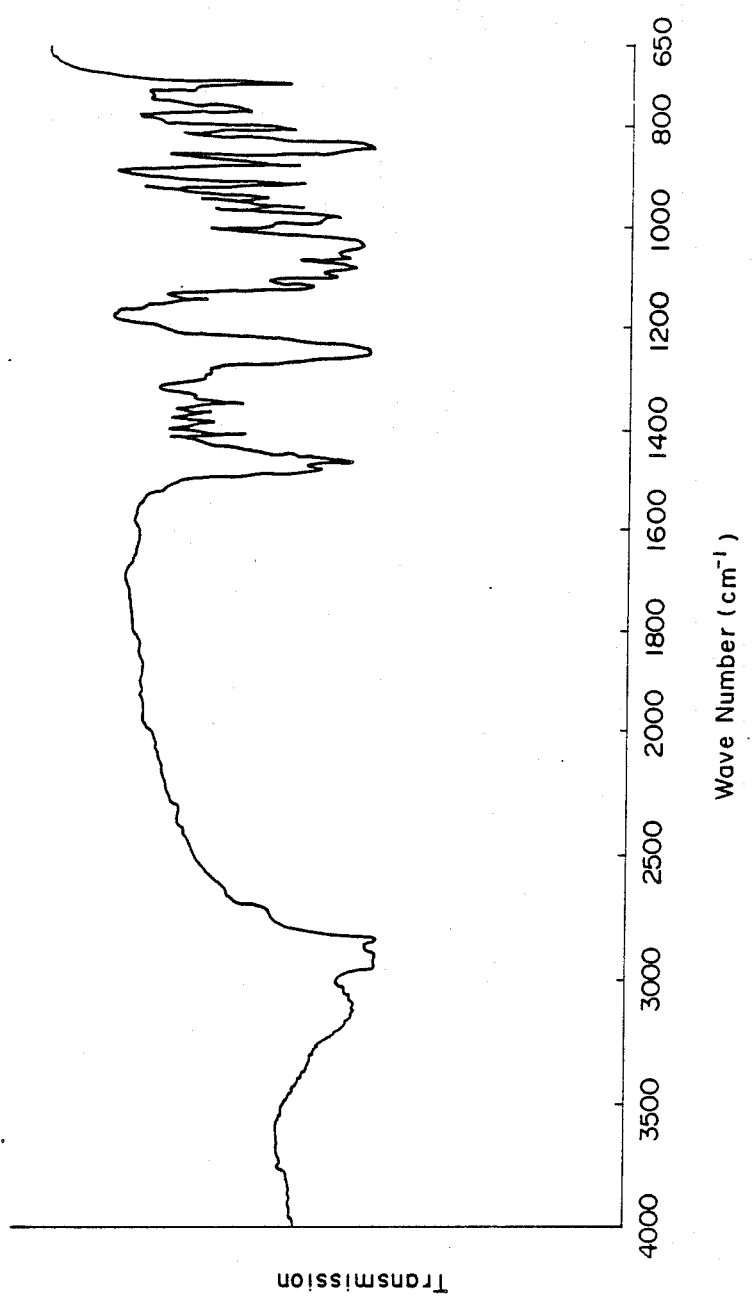

In the phosphoric ester represented by the formula (I) according to this invention, linear or branched alkyl or alkenyl group having 1 to 36 carbon atoms represented by $R_1$ can include, for examnple, methyl, ethyl, butyl, octyl, decyl, dodecyl, tetradecyl, hexadecyl, octadecyl, docosyl, tetracosyl, triacontyl, 2-ethylhexyl, 2-octyldodecyl, 2-dodecylhexadecyl, 2-tetradecyloctadecyl, monomethyl-branched-isostearyl, octenyl, decenyl, dodecenyl, tetradecenyl, hexadecenyl, octadecenyl, dococenyl, tetracocenyl and triacontenyl groups. Those phenyl groups substituted with linear or branched alkyl groups having 1 to 15 carbon atoms can include, for example, ethylphenyl, butylphenyl, hexylphenyl, octylphenyl and nonylphenyl groups.

The phosphoric ester (I) according to this invention can be produced by the novel production process represented by the following reaction scheme.

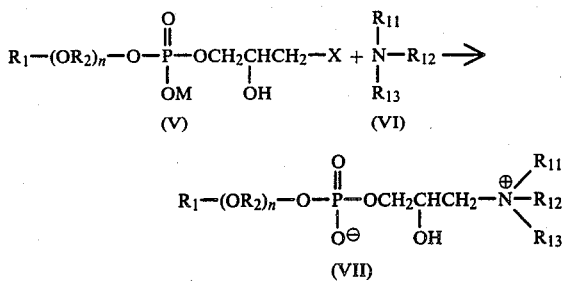

wherein X represents a halogen atom, $R_{11}$, $R_{12}$ and $R_{13}$ individually represent a hydrogen atom or a linear or branched alkyl groups having 1 to 36 carbon atoms, M represents a hydrogen atom or a salt of alkali metal or alkaline earth metal and $R_1$, $R_2$ and n have the same meanings as described above.

That is, the phosphoric ester represented by the formula (VII) comprising the compound (I) according to this invention is produced by reacting the phosphoric ester represented by the formula (V) and the amine represented by the formula (VI).

The phosphoric ester represented by the general formula (V) obtained by any of known processes may be usable herein and it can be produced easily and industrially, for example, by reacting a monoalkali metal salt of the phosphoric ester at high purity proposed by the present inventors with epihalohydrin.

Specifically, it can be produced easily, as shown by the following reaction scheme, by reacting a monoalkali metal salt of phosphoric monoester represented by the general formula (VIII) with an epihalohydrin represented by the formula (IX) and optionally acidifying and, further, neutralizing with a base.

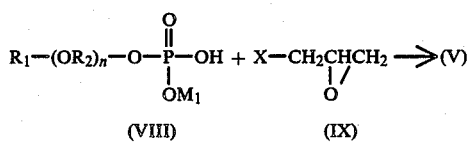

wherein $R_1$, $R_2$, $M_1$, X and n have the same meanings as described above.

The amines represented by the formula (VI) can include, for example, triethylamine, tributylamine, tripentylamine, trihexylamine, trioctylamine, tridecylamine, tridodecylamine, dimethyloctylamine, dimethyldecylamine, dimethyldodecylamine, dimethyltetradecylamine, dimethylhexadecylamine, dimethyloctadecylamine, didodecylmonomethylamine, 2-hexyldecyldimethylamine, 2-octyldodecyldimethylamine and monomethylbranched-isostearyldimethylamine.

In the reaction of the phosphoric ester (V) and the amine (VI), the amine (VI) is preferably reacted in an amount of 1 to 10 mol and, particularly, 1 to 3 mol per one mole of the phosphoric ester (V).

The solvent usable for the reaction is preferably an inert polar solvent including, for example, water, methyl alchol, ethyl alcohol and 2-propanol either solely or in admixture.

The reaction is preferably conducted at a temperature from 30° to 100° C. and particularly from 60° to 90° C.

The thus obtained reaction solution contains, in addition to the aimed compound represented by the formula (VII), inorganic salts as the by-product or unreacted amine depending on the reaction molar ratio. The reaction product obtained in this way can be used as such depending on the purpose of use, or it may be formed into a high purity product by way of a further purification. For instance, in the case of dodecyl 2-hydroxy-3-N,N-dimethyl-N-dodecylammoniopropyl phosphate ($R_1=R_{11}=C_{12}H_{25}$, $R_{12}=R_{13}=CH_3$, n=0 in the compound of the formula (VII)), aimed product at high purity can be obtained by reacting sodium dodecyl 2-hydroxy-3-chloropropyl phosphate with dimethyl dodecylamine in a mixed solvent of water and ethyl alcohol, then distilling off the solvent and removing water, adding ethyl alcohol and filtering out insoluble sodium chloride, adding the solution to a great amount of acetone thereby depositing dodecyl 2-hydroxy-N,N-dimethyl-N-dodecylammoniopropyl phosphate.

Further, as another method, purification is also possible by electrical dialysis using ion exchange membranes. Specifically, when ionic compounds are removed by electrical means using commercial ion exchange membranes, for example, cationic exchange membranes such as 66-5T (manufactured by Tokuyama Soda) and CMV (manufactured by Asahi Glass) or anionic exchange membranes such as ACH-45-T (manufactured by Tokuyama Soda) and AMV (manufactured by Asahi Glass), since only the amphoteric phosphoric ester (VII) in the reactin product is left while other impurities are eliminated, phosphoric ester (VII) at high purity can be obtained after distilling off the solvent from the residue.

In the reaction for the production of starting phosphoric ester (V), a small amount of phosphoric ester represented by the following general formula (X) may sometime be formed in addition to the phosphoric ester of the formula (V) depending on the reaction conditions:

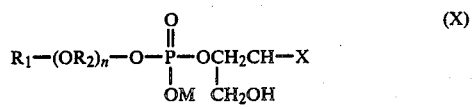

wherein $R_1$, $R_2$, M, X and n have the same meanings as described above.

Accordingly, when the reaction with the amine (VI) is conducted by using the compound represented by the formula (V) obtained by utilizing the reaction, a small amount of the compound represented by the formula (XI) may also be formed depending on the case:

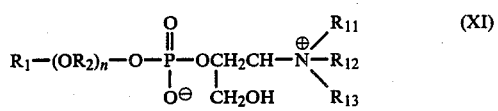

wherein $R_1$, $R_2$, $R_{11}$, $R_{12}$, $R_{13}$ and n have the same meanings as described above.

Phosphoric ester (I) according to this invention contained in the phosphoric ester (VII) obtained as described above is excellent in the surface tension and foaming property and gives extremely low stimulus to the skin, so that it can be used as detergent compositions, cosmetic compositions, emulsifiers, dispersants and anti-static agents.

This invention will now be described referring to Examples.

EXAMPLE 1

50 g (0.13 mol) of sodium dodecyl 2-hydroxy-3-chloropropyl phosphate was charged into a reactor, to which 210 ml of water and 16.6 ml of ethyl alcohol were added and dissolved at an elevated temperature of 80° C. Then, 28.8 g (0.13 mol, 97% purity) of dimethyldodecyl amine was added at that temperature and reacted for 12 hours, when the chlorine ion amount in the reaction system coincided with the total chlorine amount which indicates the completion of the reaction. The reaction mixture was dissolved into 4000 ml of ethyl alcohol and, after distilling off the solvent under a reduced pressure and removing water, 400 ml of ethyl alcohol was added and insoluble sodium chloride was removed by filtration. The product was dropped into 4000 ml of acetone. Crystals were collected by filtration and dried under a reduced pressure to obtain 64.5 g of dodecyl 2-hydroxy-3-N,N-dimethyl-N-dodecylammoniopropyl phosphate (yield 91.9%).

$^1$H NMR[δ(ppm), standard specimen: Si(CH$_3$)$_4$]: 0.9(t, 6H, —CH$_2$(CH$_2$)$_{10}$CH$_3$X2); 1.3(broad s, 40H, —CH$_2$(CH$_2$)$_{10}$CH$_3$X2); 3.2(s̄, 6H, N(CH$_3$)$_2$); 3.3–4.0(-broad, 10H,

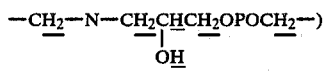

$^{13}$C NMR:

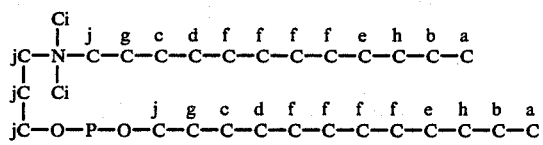

δ(ppm) a: 14.4, b: 23.7, c: 27.0, d: 27.4 e: 29.2, f: 30.8, g: 32.2, h: 3.31 i: 50.4, j: 67.1.

IR(KBr): Figure
Elementary analysis:

|  | C (%) | H (%) | P (%) | N (%) | Na (%) | Cl (%) |
|---|---|---|---|---|---|---|
| Found | 63.96 | 11.45 | 5.8 | 2.59 | 0.29 | 0.47 |
| Calculated | 65.01 | 11.66 | 5.8 | 2.61 | 0.00 | 0.00 |

EXAMPLE 2

Sodium dodecyl 2-hydroxy-3-chloropropyl phosphate was charged in an amount of 50 g (0.13 mol) into a reactor, to which 105 ml of water and 8.3 ml of ethyl alcohol were added and dissolved at an elevated temperature of 80° C. Then, 34.6 g (0.13 mol) of trihexylamine was added at that temperature and reacted for 12 hours, when the chlorine ion amount in the reaction system coincided with the total chlorine amount which indicates the completion of the reaction. The reaction mixture was dissolved into 4000 ml of ethyl alcohol and, after distilling off the solvent under a reduced pressure and removing water, 400 ml of ethyl alcohol was added and insoluble sodium chloride was removed by filtration and the product was dropped into 4000 ml of acetone. Crystals were collected by filtration and dried under a reduced pressure to obtain 73.9 g of dodecyl 2-hydroxy-3-N,N,N-trihexylammoniopropyl phosphate (yield 95.8%).

Elementary analysis:

|  | C (%) | H (%) | P (%) | N (%) | Na (%) | Cl (%) |
|---|---|---|---|---|---|---|
| Found | 66.89 | 11.34 | 5.2 | 2.35 | 0.19 | 0.30 |
| Calculated | 67.31 | 11.47 | 5.3 | 2.38 | 0.00 | 0.00 |

EXAMPLE 3

Sodium butyl 2-hydroxy-3-chloropropyl phosphate was charged in amount of 50 g (0.19 mol) into a reactor, to which 105 ml of water and 8.3 ml of ethyl alcohol were added and dissolved at an elevated temperature of 90° C. Then, 60.6 g (0.19 mol) of dimethyl-2-octyldodecylamine was added at that temperature and reacted for 8 hours, when the chlorine ion amount in the reaction system coincided with the total chlorine amount which indicates the completion of the reaction. After diluting the reaction mixture with 1000 ml of water, it was passed through an electrical dialyzing device to desalt ionic impurities and further distill off the solvent to obtain 90.1 g of butyl-2-hydroxy-3-(dimethyl-2-octyldodecylammonio)propyl phosphate (yield 90.3%).

Elementary analysis:

|  | C (%) | H (%) | P (%) | N (%) | Na (%) | Cl (%) |
|---|---|---|---|---|---|---|
| Found | 63.89 | 11.46 | 5.7 | 2.58 | 0.11 | 0.28 |
| Calculated | 65.01 | 11.66 | 5.8 | 2.61 | 0.00 | 0.00 |

EXAMPLE 4

Sodium trioxyethylenedodecyl 2-hydroxy-3-chloropropyl phosphate was charged in an amount of 10 g (0.019 mol) into a reactor, to which 21 ml of water and 1.7 ml of ethyl alcohol were added and dissolved at an elevated temperature of 90° C. Then, 7.0 g (0.019 mol) of didodecylmonomethylamine was added at that temperature and reacted for 8 hours, when the chlorine ion amount in the reaction system coincided with the total chlorine amount which indicates the completion of the reaction. When the reaction product was subjected to HPLC analysis (High Performance Liquid Chromatography, hereinafter simplified in this way), peaks corresponding to the new products were observed. The product was fractionated by HPLC and the solvent was distilled off to obtain 14.8 g of trioxyethylene dodecyl 2-hydroxy-3-N,N-didodecyl-N-methylammoniopropyl phosphate (yield 94.7%).

Elementary analysis:

|  | C (%) | H (%) | P (%) | N (%) | Na (%) | Cl (%) |
|---|---|---|---|---|---|---|
| Found | 66.87 | 11.54 | 3.8 | 1.68 | 0.05 | 0.08 |
| Calculated | 67.19 | 11.77 | 3.8 | 1.70 | 0.00 | 0.00 |

EXAMPLE 5

Potassium nonylphenyl 2-hydroxy-3-chloropropyl phosphate was charged in an amount of 10 g (0.023 mol) into a reactor, to which 20 ml of water and 20 ml of ethyl alcohol were added and dissolved at an elevated temperature of 90° C. Then, 4.9 g (0.023 mol) of dimethyldodecylamine was added at that temperature and reacted for 8 hours, when the chlorine ion amount in the reacdtion system coincided with the total chlorine amount which indicates the completion of the reaction.

When the reaction product was subjected to HPLC analysis, peaks corresponding to the new products were observed. The product was fractionated by HPLC and the solvent was distilled off to obtain 12.8 g of nonylphenyl-2-hydroxy-3-N,N-dimethyl-N-dodecylammoniopropyl phosphate (yield 96.8%).

Elementary analysis:

|  | C (%) | H (%) | P (%) | N (%) | K (%) | Cl (%) |
| --- | --- | --- | --- | --- | --- | --- |
| Found | 67.13 | 10.26 | 5.3 | 2.38 | 0.05 | 0.05 |
| Calculated | 67.45 | 10.61 | 5.4 | 2.46 | 0.00 | 0.00 |

EXAMPLE 6

Sodium dodecyl 2-hydroxy-3-chloropropyl phosphate acid was charged in an amount of 30 g (0.079 mol) into a reactor, to which 65 ml of water and 5.0 ml of ethyl alcohol were added and dissolved under an elevated temperature of 80° C. Then, 8.0 g (0.079 mol) of triethylamine was added at that temperature and reacted for 8 hours, when the chlorine ion amount in the reaction system coincided with the total chlorine amount which indicates the completion of the reaction. After diluting the reaction mixture with 1000 ml of water, it was passed through an electrical dialyzing device to desalt ionic impurities and further distill off the solvent to obtain 32.1 g of dodecyl 2-hydroxy-3-N,N,N-triethylammoniopropyl phosphate (yield 96.2%).

Elementary analysis:

|  | C (%) | H (%) | P (%) | N (%) | Na (%) | Cl (%) |
| --- | --- | --- | --- | --- | --- | --- |
| Found | 59.12 | 10.83 | 7.3 | 3.33 | 0.08 | 0.12 |
| Calculated | 59.55 | 10.95 | 7.3 | 3.31 | 0.00 | 0.00 |

REFERENCE EXAMPLE

The following compounds were obtained in the same manner as in Example 1.

(1) Dodecyl 2-hydroxy-3-N,N,N-trimethylammoniopropyl phosphate

Elementary analysis:

|  | C (%) | H (%) | N (%) | P (%) |
| --- | --- | --- | --- | --- |
| Found | 56.6 | 10.4 | 3.6 | 7.4 |
| Calculated | 56.7 | 10.6 | 3.7 | 8.1 |

(2) Hexadecyl 2-hydroxy-3-N,N,N-trimethylammoniopropyl phosphate

Elementary analysis:

|  | C (%) | H (%) | N (%) | P (%) |
| --- | --- | --- | --- | --- |
| Found | 60.4 | 10.9 | 3.3 | 6.9 |
| Calculated | 60.3 | 11.1 | 3.2 | 7.1 |

(3) Octyl 2-hydroxy-3-N,N,N-trimethylammoniopropyl phosphate

Elementary analysis:

|  | C (%) | H (%) | N (%) | P (%) |
| --- | --- | --- | --- | --- |
| Found | 51.9 | 9.8 | 4.4 | 9.5 |
| Calculated | 51.7 | 9.9 | 4.3 | 9.5 |

(4) Trioxyethylenedodecylether 2-hydroxy-3-N,N,N-trimethylammoniopropyl phosphate Elementary analysis:

|  | C (%) | H (%) | N (%) | P (%) |
| --- | --- | --- | --- | --- |
| Found | 56.3 | 10.0 | 2.7 | 5.9 |
| Calculated | 56.2 | 10.2 | 2.7 | 6.0 |

What is claimed is:

1. A phosphoric ester represented by the following general formula (I)

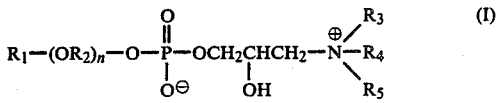

wherein $R_1$ represents a linear or branched alkyl or alkenyl group having 1 to 36 carbon atoms, or a phenyl group substituted with a linear or branched alkyl group having 1 to 15 carbon atoms, $R_2$ represents an alkylene group having 2 to 3 carbon atoms, $R_3$, $R_4$ and $R_5$ individually represent a hydrogen atom or a linear or branched alkyl group having 1 to 36 carbon atoms providing that any one of $R_3$, $R_4$ and $R_5$ has from 12 to 36 carbon atoms, and n is a number from 0 to 30.

2. A compound according to claim 1, which is dodecyl 2-hydroxy-3-N,N-dimethyl-N-dodecylammoniopropyl phosphate.